(12) United States Patent
Tkach

(10) Patent No.: US 10,292,511 B2
(45) Date of Patent: May 21, 2019

(54) METHODS, SYSTEM AND APPARATUS TO IMPROVE MOTIVATION AND CONTROL WHEN TAKING MEALS AND TO AUTOMATE THE PROCESS OF MONITORING NUTRITION

(71) Applicant: Anatoliy Tkach, Atlantic Highlands, NJ (US)

(72) Inventor: Anatoliy Tkach, Atlantic Highlands, NJ (US)

( * ) Notice: Subject to any disclaimer, the term of this patent is extended or adjusted under 35 U.S.C. 154(b) by 0 days.

(21) Appl. No.: 15/654,113

(22) Filed: Jul. 19, 2017

(65) Prior Publication Data
US 2018/0098649 A1 Apr. 12, 2018

Related U.S. Application Data

(60) Provisional application No. 62/405,194, filed on Oct. 6, 2016.

(51) Int. Cl.
| | |
|---|---|
| *A47G 19/30* | (2006.01) |
| *G06F 19/00* | (2018.01) |
| *A47G 19/02* | (2006.01) |
| *A61B 5/00* | (2006.01) |
| *G16H 20/60* | (2018.01) |
| *A47G 23/14* | (2006.01) |
| *A61B 5/11* | (2006.01) |

(52) U.S. Cl.
CPC .......... *A47G 19/025* (2013.01); *A61B 5/681* (2013.01); *G06F 19/3475* (2013.01); *G16H 20/60* (2018.01); *A47G 19/30* (2013.01); *A47G 23/14* (2013.01); *A61B 5/1114* (2013.01)

(58) Field of Classification Search
CPC .................................................... A47G 19/025
USPC ........................................................ 340/666
See application file for complete search history.

(56) References Cited

U.S. PATENT DOCUMENTS

| | | | |
|---|---|---|---|
| 3,244,859 A * | 4/1966 | Whiteford ................. | F24C 7/06 165/133 |
| 2015/0260566 A1* | 9/2015 | Conder .............. | G01G 19/4144 177/25.13 |
| 2016/0018255 A1* | 1/2016 | Fang ....................... | H04W 4/80 177/25.13 |

(Continued)

*Primary Examiner* — Santiago Garcia
(74) *Attorney, Agent, or Firm* — Anna Vishev

(57) ABSTRACT

A meal consumption monitoring and control system is disclosed. The system includes a flat profile scale serving as a coaster for a plate, a cup, or a glass enabled with Bluetooth or other type of wireless connectivity. The scale is connected to an accompanying mobile application installed on a mobile device. The mobile application is connected to the accompanying server-side cloud bases software application. The method for motivating children to consume meal in whole and without significant interruptions includes displaying a children content on the mobile device during the meal consumption, pausing the content when there is a significant delay registered in the meal consumption process, and resuming the content and/or providing certain awards to the child when the child resumes taking meal. The method for automatically controlling the consistency of the eater's nutrition includes collecting meal descriptions and weight data at every meal taking session, and storing the collected data on the cloud for further access by the eaters and/or their parents/guardians.

5 Claims, 1 Drawing Sheet

(56) References Cited

U.S. PATENT DOCUMENTS

| | | | |
|---|---|---|---|
| 2016/0112684 A1* | 4/2016 | Connor | G01N 33/02 348/158 |
| 2016/0138962 A1* | 5/2016 | Cartwright | G01G 21/22 177/1 |
| 2016/0143582 A1* | 5/2016 | Connor | A61B 5/4866 600/301 |
| 2016/0192619 A1* | 7/2016 | Gibbs | A01K 5/00 119/61.57 |
| 2016/0270574 A1* | 9/2016 | Dekar | A47G 21/08 |
| 2017/0173262 A1* | 6/2017 | Veltz | A61M 5/1723 |
| 2017/0184442 A1* | 6/2017 | Satish | G01G 17/04 |
| 2017/0328764 A1* | 11/2017 | Tsai | G01G 19/4146 |
| 2018/0073915 A1* | 3/2018 | Finnance | G01G 19/52 |
| 2018/0106663 A1* | 4/2018 | Ashmore | G01G 19/4146 |

\* cited by examiner

METHODS, SYSTEM AND APPARATUS TO IMPROVE MOTIVATION AND CONTROL WHEN TAKING MEALS AND TO AUTOMATE THE PROCESS OF MONITORING NUTRITION

BACKGROUND

The present invention is in the field of nutrition. More particularly, the present invention is in the technical field of the equipment used to serve meals.

In the process of feeding preschoolers and school-age children up to 8 years old, it is important to make sure that the child would consume the appropriate amount of the served meal, and within the adequate amount of time. Existing meal serving equipment such as dinner-plates, soup-plates, cups and glasses does not provide built in means to reduce the number of interruptions during the time the child is taking meal. Moreover, in order to make the meal taking process more attractive for the child, parents/guardians often install an entertainment device such as tablet PC or a mobile phone in front of a child, so the child's attention is often switched to the show performed on that device for an uncontrolled amount of time. The existing meal serving equipment does not provide built-in means to automatically measure and memorize the amount of certain food consumed by the child.

In the process of meal taking by both adults and children, it is also important for the eater or their parents/guardians to control the amount of certain nutrition ingredients consumed over time, as well as to receive information about the number of calories consumed.

The existing meal serving equipment does not provide built-in means to automatically measure and memorize the amount and/or calorie content of the food consumed.

SUMMARY

Therefore, it is a first object of this invention to increase the level of motivation for children to consume the meal in whole and without interruptions. It is a second object of this invention to provide automated control over the amounts of nutrition ingredients and the number of calories consumed by the eater over time.

The present invention is a combination of the following hardware and software components, also referred to as "OmNomScale": a flat profile electronic scale installed on the table in front of the eater and serving as a coaster for a plate, a cup, or a glass. The electronic scale is connected to a mobile application software installed on a mobile device. The connection being accomplished via a Bluetooth or other type of wireless connection. The mobile application software is, in turn, connected to a cloud-based data storage software.

The present invention is aimed to improve the level of motivation for the child to consume the meal in whole and without interruptions, as well as to provide eaters and/or their parents/guardians with automated control over the amounts of nutrition ingredients and the number of calories consumed by the eater over time.

The core component of the invention is a flat electronic scale installed on the table in front of the eater and serving as a coaster for the plate, cup, or a glass. Being switched on, the scale pairs with the accompanied mobile application running on the mobile device installed in front of the eater behind the scale.

In case of child feeding application, parent/guardian puts the empty plate on the scale, and the mobile application registers the weight reading over Bluetooth or other type of wireless connection. After that, the parent/guardian fills the plate with meal and returns the plate to the scale—the application registers the meal weight. Parent/guardian enters the meal title into the application, seats the child in front of the meal, and starts the show such as a cartoon or a video clip on the application. The application is monitoring the weight readings transmitted to it from the scale over Bluetooth or other type of wireless connection. The show pauses automatically in case there is no weight decrease during certain preset amount of time. In that case, the attractive cartoon character pops up on the application asking the eater aloud to resume eating meal. The character could also offer certain award for the next portion of the meal taken. When the next weight decrease is registered, the show releases from the pause. The process continues until the certain preset level of the meal consumption is achieved. At that point, the meal taking session stops, and the application sends the total weight of the meal taken to the cloud based software application for further access by the parents/guardians.

The effect such as improvement of the child's motivation is achieved by making the child interested in continuing the show and/or to receive the award.

The effect such as automated control over the amounts of nutrition ingredients and the number of calories consumed by the child over time is achieved by collecting all meal taking sessions data on the cloud and making this data available to the parent/guardian.

In case of meal taking by adult, eater puts the empty plate on the scale, and the mobile application registers the weight reading over Bluetooth or other type of wireless connection. After that, the eater fills the plate with meal and returns the plate to the scale—the application registers the meal weight. Eater enters the meal title into the application and starts eating. The application is monitoring the weight readings transmitted to it from the scale over Bluetooth or other type of wireless connection. The process continues until the eater commands the application to end the measurement session. After that, the application shows the figures representing the amounts of nutrition ingredients and the number of calories consumed by the eater.

The effect such as automated control over the amounts of nutrition ingredients and the number of calories consumed by the eater over time is achieved by collecting all meal taking sessions data on the cloud and making this data available to the eater allowing them to manage their health conditions by means of balanced nutrition practices and weight control workouts.

The above aspects, advantages and features are of representative embodiments only. It should be understood that they are not to be considered limitations on the invention as defined by the claims. Additional features and advantages of the invention will become apparent in the following description, from the drawings, and from the claims.

BRIEF DESCRIPTION OF THE DRAWINGS

For a more complete understanding of the present disclosure and its advantages, reference is made to the following descriptions, taken in conjunction with the accompanying drawings; in which.

DETAILED DESCRIPTION

Figure 1:
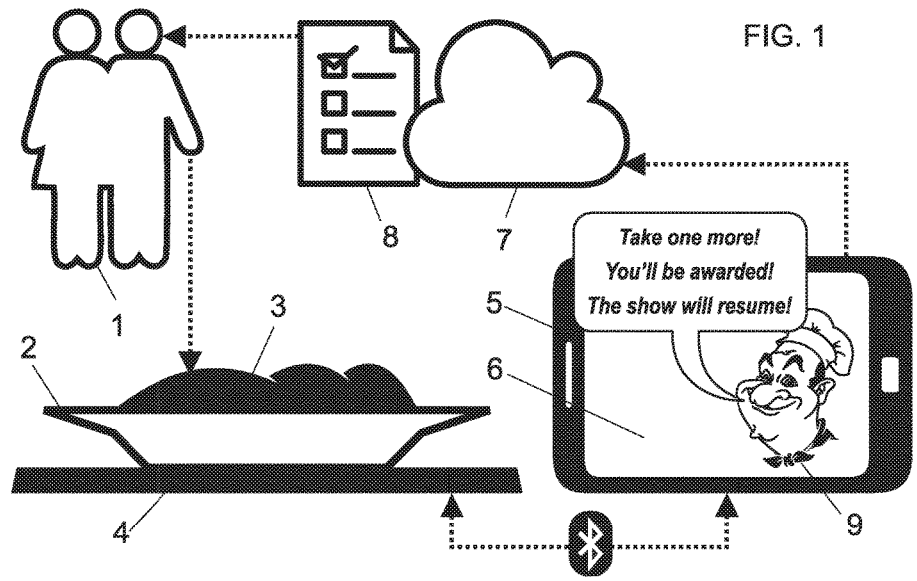
FIG. 1 is a schematic diagram of an exemplary workflow for child feeding.

As an exemplary embodiment depicted on FIG. 1, a meal is served to the child in the plate put on the scale installed on the table in front of a child. The accompanying tablet PC is also installed on the table next to the plate.

As depicted on FIG. 1, a parent 1 turns on the scale 4 and pairs it over Bluetooth with the mobile application 6 previously started by the parent 1 on the tablet 5. After the pairing process is complete, the application 6 shows its readiness to receive the empty plate 2 weight reading.

Parent 1 puts the empty plate 2 on the scale 4. The application 6 registers the empty plate 2 weight reading, and reports readiness to receive the meal 3 weight reading. Parent 1 enters a meal title and description into the application 6, fills the empty plate 2 with the meal 3, and puts the plate 2 with the meal 3 back to the scale 4. The application 6 registers the total weight, calculates the meal 3 weight, and reports readiness to start continuous weigh readings. Parent 1 seats the child in front of the meal 3, and initiates children content, such as a cartoon or a video clip, on the tablet 5 using the application 6. Starting from that point, the application 6 reads the weight on the scale 6 over Bluetooth for every 2 seconds (this value is available to be pre-set by the parent 1 in the application 6 settings). In case there is no weight decrease over 20 grams (this value is available to be pre-set by the parent 1 in the application 6 settings) during 30 seconds (this value is available to be pre-set by the parent 1 in the application 6 settings), the show pauses automatically. In that case, the attractive cartoon character 9 pops up on the application asking the eater aloud to resume eating meal. The character 9 could also offer certain award for the next portion of the meal taken. When the next validated weight decrease is registered by the application 6, the show releases from the pause. The process continues until the certain preset level such as 75% (this value is available to be pre-set by the parent 1 in the application 6 settings) of the meal consumption is achieved. At that point, the meal taking session stops automatically, and the application 6 sends the total weight of the meal taken 8 to the cloud based server software application 7 for further access by the parents 1.

The accumulative data 8 about nutrition ingredients and calories consumed by the child is always available to the parent 1 on the mobile application 6 or through the cloud based server application 7 for establishing appropriate balanced nutrition practices and weight control activities.

Figure 2:
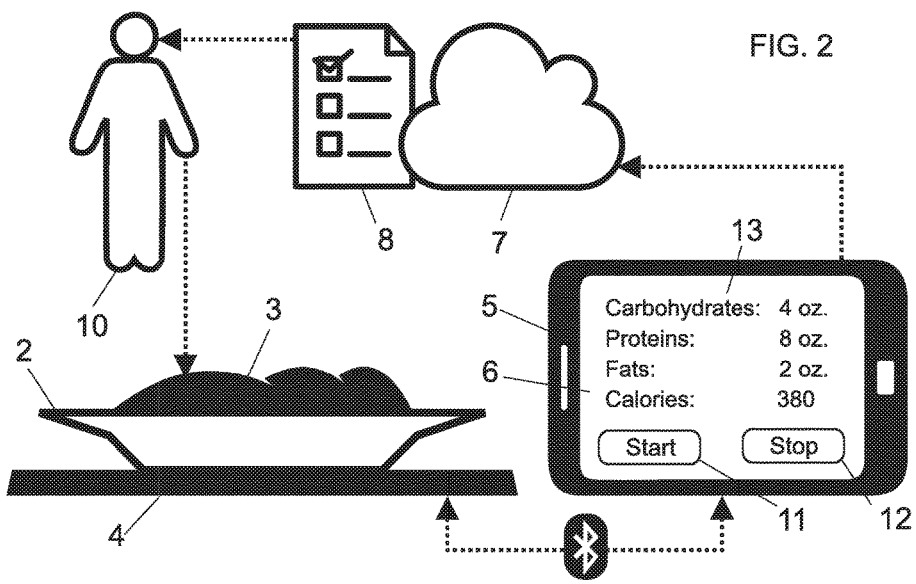
FIG. 2 is a schematic diagram of an exemplary workflow for an adult meal taking.

As an exemplary embodiment depicted on FIG. 2, a meal is served to an adult eater on a plate put on the scale 4 installed on the table in front of an eater. The accompanying mobile device, i.e., tablet computer 5, is also available for the eater to operate.

As depicted on FIG. 2, eater 10 turns on the scale 4 and pairs it over Bluetooth with the mobile application 6 previously started by the eater 10 on the tablet 5. After the pairing process is complete, the application 6 shows its readiness to receive the empty plate 2 weight reading.

Eater 10 puts the empty plate 2 on the scale 4. The application 6 registers the empty plate 2 weight reading, and reports readiness to receive the meal 3 weight reading. Eater 10 enters a meal title and description into the application 6, fills the empty plate 2 with the meal 3, and puts the plate 2 with the meal 3 back to the scale 4. The application 6 registers the total weight, calculates the meal 3 weight, and reports readiness to start continuous weigh readings. Eater 10 taps on the Start button 11 and starts taking meal. After meal is taken, the Eater 10 taps on the Stop button 12. As a result, the mobile application 6 reads the weight 8 from the scale 4 over Bluetooth and saves it on the cloud based server software application 7 for future access by the eater 10. Then, the mobile application 6 retrieves the corresponding consumed nutrition ingredients and calorie content data from the cloud based server software application 7, and shows that data to the eater 10 in the data presentation area 13 of the mobile application 6. The accumulative nutrition ingredients and calories consumed data 8 is always available to the eater 10 on the mobile application 6 for establishing appropriate balanced nutrition practices and weight control workouts.

In operation, the scale 4 is available for purchase in retail stores. The mobile application 6 is available for download from all existing app stores for iOS, Android, and Windows mobile operating systems. The server-side cloud based application 7 is available for eaters and/or their parents/guardians to subscribe on a provided website. As a result, eaters (both children and adults) and/or their parents/guardians gain the following beneficial effects:

Children get fun eating food, thus improving their motivation to consume meal in whole and without significant interruptions.

Eaters and/or their parents/guardians stay in control of their or their child's nutrition thus improving their health conditions.

In the preceding specification, the invention has been described with reference to specific exemplary embodiments thereof. It will however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A meal consumption monitoring and control system, comprising:

a flat profile scale configured as a coaster to be positionable under a dish, said scale being enabled with a wireless connectivity and being configured to continuously measure a weight of a meal in said dish;

a mobile device having a mobile application installed thereon, said mobile application being selectively connectable to the flat profile scale via said wireless connectivity; and a server having a server-side cloud based software application; said mobile application being selectively connectable to the server-side cloud based software application;

wherein said mobile application is configured to initiate a predetermined entertainment content on said mobile device when prompted by a user, wherein said mobile application is further configured to stop said predetermined entertainment content when said weight of said meal does not change for a predetermined period of time, wherein said mobile application is further configured to provide a voice prompt to an eater after said predetermined entertainment content is stopped, and wherein said mobile application is further configured to resume said predetermined entertainment content when said weight of said meal begins reducing again.

2. The system of claim 1, wherein said mobile application is configured to determine a nutritional value of a consumed portion of said meal and to communicate said nutritional value to said server-side cloud based software application, and wherein said server-side cloud based software application is configured to store said nutritional value on said server.

3. The method for motivating eaters to consume a meal, the method comprising the steps of:
providing a flat profile scale and positioning said scale under a dish, said scale being enabled with a wireless connectivity;
providing a mobile device with a mobile application installed thereon, the mobile application being configured to initiate a predetermined entertainment content on said mobile device when prompted by a user;
selectively connecting said mobile application to the flat profile scale via said wireless connectivity;
using said flat profile scale to continuously measure a weight of a meal in said dish;
conveying said weight of said meal to said mobile application via said wireless connectivity;
using said mobile application to stop said predetermined entertainment content when said weight of said meal does not change for a predetermined period of time;
using said mobile application to provide a voice prompt to an eater after said predetermined entertainment content is stopped; and
using said mobile application to resume said predetermined entertainment content when said weight of said meal begins reducing again.

4. The method of claim 3, further comprising steps of providing a server having a server-side cloud based software application; and selectively connecting said mobile application to the server-side cloud based software application.

5. The method of claim 4, further comprising steps of using said mobile application to determine a nutritional value of a consumed portion of said meal; communicating said nutritional value to said server-side cloud based software application; and using said server-side cloud based software application to store said nutritional value on said server.

* * * * *